(12) United States Patent
Schuler et al.

(10) Patent No.: US 7,818,142 B2
(45) Date of Patent: Oct. 19, 2010

(54) METHOD AND APPARATUS FOR PREDICTIVE, CONTEXT-AWARE, AND NETWORKED EXPOSURE TIME MONITORING

(75) Inventors: Francesca Schuler, Des Plaines, IL (US); Krishna Jonnalagadda, Algonquin, IL (US)

(73) Assignee: Motorola Mobility, Inc., Libertyville, IL (US)

( * ) Notice: Subject to any disclaimer, the term of this patent is extended or adjusted under 35 U.S.C. 154(b) by 371 days.

(21) Appl. No.: 11/946,540

(22) Filed: Nov. 28, 2007

(65) Prior Publication Data

US 2009/0138244 A1    May 28, 2009

(51) Int. Cl.
*G04G 5/00* (2006.01)
*G04F 1/00* (2006.01)

(52) U.S. Cl. .................. 702/176; 340/600; 340/601; 702/3; 702/179; 703/2

(58) Field of Classification Search .................. 703/2; 702/3, 176, 179, 189; 340/600, 601
See application file for complete search history.

(56) References Cited

U.S. PATENT DOCUMENTS

| 4,348,664 | A | * | 9/1982 | Boschetti et al. ............. 340/600 |
| 5,036,311 | A | | 7/1991 | Moran et al. |
| 5,107,123 | A | * | 4/1992 | Shi ............................. 250/372 |
| 5,365,068 | A | | 11/1994 | Dickerson |
| 5,382,986 | A | | 1/1995 | Black et al. |
| 5,995,862 | A | * | 11/1999 | Gallorini ..................... 600/407 |
| 7,073,129 | B1 | | 7/2006 | Robarts et al. |

| 2004/0031927 | A1 | | 2/2004 | Tsai et al. |
| 2004/0149921 | A1 | | 8/2004 | Smyk |
| 2005/0264752 | A1 | | 12/2005 | Howell et al. |
| 2006/0001827 | A1 | | 1/2006 | Howell et al. |
| 2006/0151709 | A1 | | 7/2006 | Hahl |
| 2006/0250261 | A1 | | 11/2006 | Henrie et al. |
| 2007/0073487 | A1 | * | 3/2007 | Albright et al. ................. 702/3 |

FOREIGN PATENT DOCUMENTS

| EP | 1653204 A1 | 5/2006 |
| WO | 2004072594 A1 | 8/2004 |

OTHER PUBLICATIONS http://www2.oregonscientific.com/shop/product.asp?cid=2&scid=5&pid=644.
http:/www.partshelf.com/ci00913.html.
http:/www.wirelessalarm.com/NU300.html.
http://www.professionalequipment.com/chemical-detection-device-chameleon-starter-kit-085100/multi-gas-meters.
http://apps.em.doe.gov/OST/pubs/itsrs/itsr2104.pdf; "Wireless Remote Radiation Monitoring System".

* cited by examiner

*Primary Examiner*—Mohamed Charioui
*Assistant Examiner*—Elias Desta

(57) ABSTRACT

A method and apparatus for predictive, context-aware, and networked exposure time monitoring. The method may include storing (320), in a memory, personal information including skin phototype and sun protection factor information, obtaining (330) context related information including an activity, a location, and a time of day, and retrieving (340) environmental conditions that affect ultraviolet exposure. The environmental conditions can include weather conditions retrieved from a network. The method can also include predicting (350) ultraviolet exposure time based on the personal information, the context related information, and the environmental conditions and outputting (360) information corresponding to the ultraviolet exposure time.

18 Claims, 4 Drawing Sheets

METHOD AND APPARATUS FOR PREDICTIVE, CONTEXT-AWARE, AND NETWORKED EXPOSURE TIME MONITORING

BACKGROUND

1. Field

The present disclosure is directed to a method and apparatus for predictive, context-aware, and networked exposure time and UV ultraviolet Index monitoring. More particularly, the present disclosure is directed to ultraviolet index and exposure time monitoring and prediction based on context information and information obtained from a network.

2. Introduction

Presently, many people enjoy outdoor activities, such as hiking, skiing, soccer, beach volleyball, sporting events, festivals, picnics, and other outdoor activities. Even though people enjoy such outdoor activities, there is a growing consciousness of the dangers of overexposure to ultraviolet light from the sun. Such overexposure can result in sunburn and even skin cancer. These dangers conflict with a person's desire to engage in outdoor activities with the benefits of being outdoors. Such benefits can include exposure to fresh air, vitamin D from the sun, mitigation of seasonal affective disorder, exercise, and other benefits from outdoor activities.

To reduce the danger of overexposure to the sun a person may use an ultraviolet monitor device to keep track of exposure. Unfortunately, such devices only provide information based on current or past ultraviolet measurements. The current and past measurements may be inaccurate when conditions change. For example, a person engaging in an activity after receiving information based on past measurements may experience different conditions, such as weather, altitude, ground conditions, local environment, etc. These different conditions can dramatically increase the person's ultraviolet exposure, thus reducing permissible exposure time for the activity.

For example, a man may plan to ski for 5 hours. He can leave a ski lodge and use an ultraviolet monitor, which can notify him he has 6 hours of exposure time based on the sun protection factor of his sunscreen and based on his skin type. However, as he is lifted to the top of the ski mountain, the ultraviolet radiation can increase to the point of which permissible ultraviolet exposure time is only 1 hour. Therefore, he will dramatically increase the dangers of overexposure because his monitor gave him an inaccurate estimate.

Thus, there is a need for a method and apparatus for predictive, context-aware, and networked exposure time monitoring.

SUMMARY

A method and apparatus for predictive, context-aware, and networked exposure time monitoring. The method may include storing, in a memory, personal information including skin phototype and sun protection factor information, obtaining context related information including an activity, a location, and a time of day, and retrieving environmental conditions that affect ultraviolet exposure. The environmental conditions can include weather conditions retrieved from a network. The method can also include predicting ultraviolet exposure time based on the personal information, the context related information, and the environmental conditions and outputting information corresponding to the ultraviolet exposure time.

BRIEF DESCRIPTION OF THE DRAWINGS

In order to describe the manner in which advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

Figure 1:
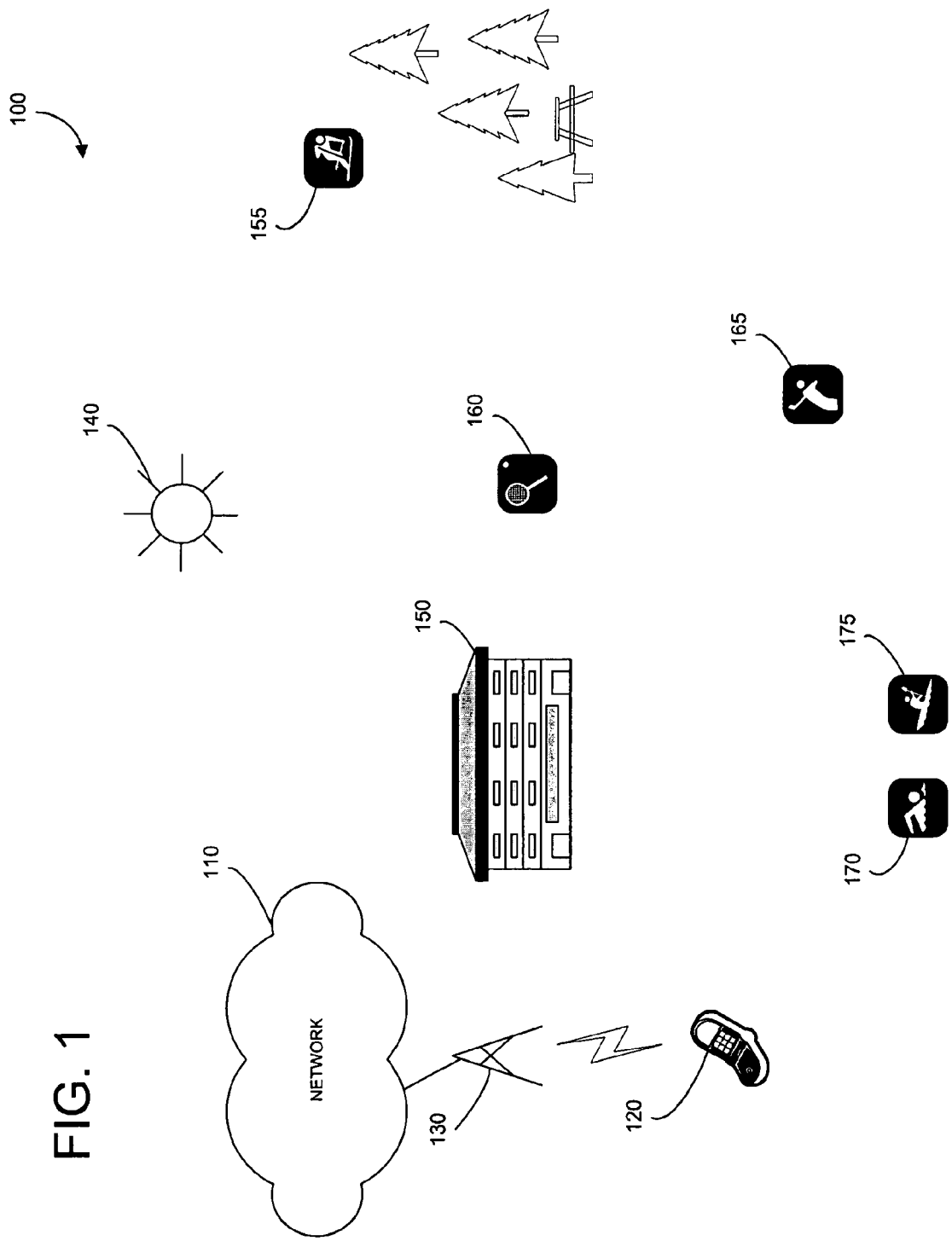
FIG. 1 illustrates an exemplary block diagram of a system in accordance with a possible embodiment.

FIG. 1 is an exemplary block diagram of a system 100 according to one embodiment. The system 100 can include a network 110, a terminal 120, and a base station 130. The terminal 120 may be a wireless communication device, such as a wireless telephone, a cellular telephone, a personal digital assistant, a pager, a personal computer, a selective call receiver, or any other device that is capable of sending and receiving communication signals on a network including wireless network. The base station 130 may be a cellular base station, a wireless local area network access point, or any other device that provides access between a wireless device and a network.

The network 110 may include any type of network that is capable of sending and receiving signals, such as wireless signals. For example, the network 110 may include a wireless telecommunications network, a cellular telephone network, a Time Division Multiple Access (TDMA) network, a Code Division Multiple Access (CDMA) network, a Wireless Local Area Network (WLAN) a satellite communications network, and other like communications systems. Furthermore, the network 110 may include more than one network and may include a plurality of different types of networks. Thus, the network 110 may include a plurality of data networks, a plurality of telecommunications networks, a combination of data and telecommunications networks and other like communication systems capable of sending and receiving communication signals.

The system 100 can also include various locations at which a user can partake in activities. For example, a user may start out at a home or a lodge 150 and then go outside to engage in activities such as skiing 155, tennis 160, golf 165, swimming 170, kayaking 175, or any other activities. While engaging in a chosen activity, the user may be exposed to ultraviolet rays from the sun 140.

In operation, the terminal 120 can store, in a memory, personal information including skin type and sun protection factor information. The terminal 120 can obtain context related information including activity information indicating an outdoor activity a user is engaging in, a location, a date, and a time of day. The terminal 120 can retrieve environmental conditions that affect ultraviolet exposure. The environmental conditions including forecast weather conditions that can be retrieved from the network 110. The terminal 120 can predict future ultraviolet exposure time based on personal information and erythemal effective radiant exposure. The erythemal effective radiant exposure can be based on solar spectral irradiance as a function of the context related information and the environmental conditions. The erythemal effective radiant exposure can also be based on erythema action spectrum, time, and a relevant wavelength of the ultraviolet rays. The terminal 120 can then output information corresponding to the ultraviolet exposure time.

Thus, the present disclosure can provide mobile devices and accessories with an integrated and networked ultraviolet measurement device linked to context aware active lifestyles software and/or an ultraviolet sensor network for predictive ultraviolet and exposure time based on activity conditions.

The system 100 can use a context aware predictive algorithm for ultraviolet index and exposure time. For example, the context can include a location, an activity, time, or other related information. The system 100 can obtain inputs on weather, ground conditions, and other related information from web services or other network sources. The system 100 can incorporate data from local, fixed, and/or mobile ultraviolet sensors, when available. The system 100 can also integrate personal information such as skin type, sun protection factor (SPF) of sun lotion, and other personal information. The system 100 can also incorporate an ultraviolet sensor on the terminal 120 and/or on accessories, such as on a headset, sunglasses, jackets, and other accessories.

For example, the system 100 can provide a networked ultraviolet monitor that retrieves appropriate context aware information from various sources to predict ultraviolet exposure and exposure time for an activity. The system 100 can predict an ultraviolet index, ultraviolet exposure, and/or exposure time based on a sensor network or sensors on other devices and/or activity context aware inputs. For example, a sensor network may be a fixed sensor network that can be maintained by an entity, such as a ski slope operator. Also, sensors on other devices can be carried by individuals and can send their data, which can be aggregated to form data from another type of sensor network. The system 100 can use context awareness for activity planning by determining exposure time based on an activity context information, such as an activity, time, a location, an altitude, ground conditions, and other context information in addition to SPF and skin type.

As another example, a user can have a skiing activity and a related time set up in an activity management application and have a device selected for ultraviolet monitoring. The device can query to see if an ultraviolet sensor network is available. If none are available the device can report current ultraviolet information and exposure time information, for example, at a lodge 150, prior to the user engaging in the activity. The device can also report worst case ultraviolet information and exposure information for the user at the activity, such as at a ski slope 155, using a model where inputs can include an activity, a time, ground conditions, cloud cover, altitude, skin type, current ultraviolet conditions, and/or a SPF of skin protection, such as sunscreen. The inputs can be entered by a user, extracted from a networked database, stored in a mobile device, or otherwise obtained. The system 100 can predict ultraviolet radiation exposure and an allowed exposure time during the activity.

If sensors are used, the user can have skiing set up in an activity management application and have a device selected for ultraviolet monitoring. The device can use its own sensor and/or query to see if other ultraviolet remote sensors are available via a sensor network, other devices, or otherwise. If other remote sensors are available, the system 100 can import sensor values, an activity, time, skin type, and a SPF of skin protection, such as sunscreen. The system 100 can predict ultraviolet radiation exposure and an allowed exposure time during an activity.

In making the predictions, the system 100 can take into account a relevant ultraviolet radiation range, such as that for UVA (315-400 nm), UVB (280-315 nm), UVC (100-280 nm). The system 100 can also take into account the fact that the earth's surface is composed of UVA and small component of UVB. The system 100 can further take into account skin phototypes, such as (1) never tans/always burns, (2) sometimes tans/usually burns, (3) usually tans, sometimes burns, and (4) always tans, rarely burns. The system 100 can further take into account the SPF, that can give an indication of sunscreen effectiveness. For example, SPF 4 can indicate that ultraviolet exposure received after spending a given time in the sun is ¼ that received in absence of any protection.

The following equations can be used to predict the exposure time:

Ultraviolet index based on an integral over an appropriate wavelength ($\lambda$) spectrum:

$$I_{UV} = k_{er} \int_{250\,nm}^{400\,nm} E_\lambda s_{er}(\lambda) d\lambda$$

Where a minimal ultraviolet index can be 0-2, a low ultraviolet index can be 3-4, a moderate ultraviolet index can be 5-6, a high ultraviolet index can be 7-8, and a very high ultraviolet index can be 10-15. $E_\lambda$ can be the solar spectral irradiance expressed in W/nm at the relevant wavelengths. The ultraviolet index can be based on a irradiance scaling factor:

$k_{er} = 40\ m^2/W$

The erythema action spectrum ($S_{er}$) can be the ability for ultraviolet radiation to produce erythema in human skin, where relevant values can be:

$s_{er}(\lambda) = 1.0$ for $250 \leq \lambda \leq 298$ nm, $s_{er}(\lambda) = 10^{0.094(298-\lambda)}$ for $298 < \lambda \leq 328$ nm, and $s_{er}(\lambda) = 10^{0.015(140-\lambda)}$ for $328 < \lambda \leq 400$ nm.

The exposure time can also be based on an erythemal effective irradiance ($E_{er}$) from an ultraviolet source:

$$E_{er} = \int_{250\,nm}^{400\,nm} E_\lambda s_{er}(\lambda) d\lambda$$

An erythemal effective radiant exposure (a.k.a. effective dose $H_{er}$) can be the time integral of erythemal effective radiance:

$H_{er} = \iint E_\lambda s_{er}(\lambda) d\lambda dt$

The dose can be expressed as an erythemal quantity received after an exposure period of t seconds:

$H = E_{er} \cdot t / \phi$

Where $\phi$ can be the numerical value in Jm² equivalent to 1 erythemal quantity. For example, a standard erythema dose (SED) can be a standardized measure of UV where 1 SED can be equivalent to an erythemal effective radiant exposure of 100 Jm². A minimal erythema dose (MED) can be a subjective measure based on reddening of skin, which can depend on individual sensitivity, skin pigmentation, elapsed time between irradiation, etc. based on observational studies. For example, MED's in subjects with skin phototypes of 1-4 may lie between erythemal effective radiant exposures of 150 Jm$^2$ to 600 Jm$^2$, which can result in 1.5-6 SED.

For example, an activity and time can be obtained. If remote sensors are not used, E*$_{er}$ can be calculated, where "*" can indicate that E$_{er}$ is modified by multipliers based on altitude, ground conditions, cloud cover, time, and other relevant variables. For example, for altitude, E*$_{er}$ can be based on (Altitude(m)/300 m*1.05)E$_{er}$. For ground conditions, E*$_{er}$ can be based on (X)E$_{er}$, where X can be 80-90% depending the surface. For cloud cover, E*$_{er}$ can be based on (X)E$_{er}$, where X can be based on cloud conditions. The multipliers can be combined based on the information available. The result can be converted to an ultraviolet index (I$_{uv}$) based on:

$$I_{UV}^* = k_{er} \int_{250\,nm}^{400\,nm} E_\lambda^* s_{er}(\lambda) d\lambda$$

H*$_{er}$ can be calculated with multipliers considering skin type and a sun protection factor based on:

$$H^*_{er} = \iint E^*_\lambda s_{er}(\lambda) d\lambda dt$$

Thus, the exposure time can be predicted based on:

$$H^*_{er} = E^*_{er} \cdot t/\phi$$

If sensors are available, actual ultraviolet values can be used with the above formulas. A recommendation of various sun protection precautions can be provided to the user in textual, graphical, or audible format. For example, the terminal 120 can recommend relevant articles of clothing, sunglasses, sun lotion, periods of shade, exposure time, and/or even staying indoors. The terminal 120 can also provide a prediction of the ultraviolet index at the location of a desired activity.

Figure 2:
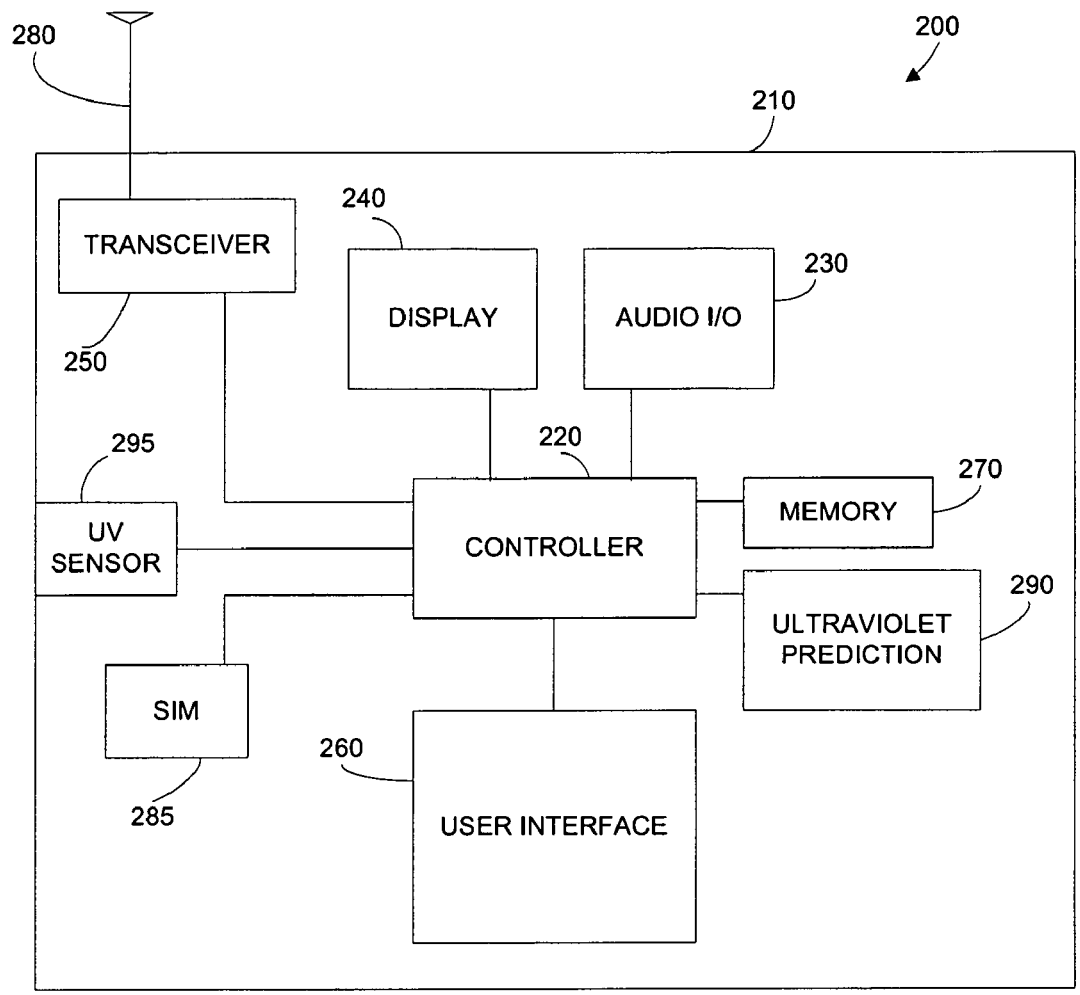
FIG. 2 illustrates an exemplary block diagram of a wireless communication device in accordance with a possible embodiment.

FIG. 2 is an exemplary block diagram of a wireless communication device 200, such as the terminal 120, according to one embodiment. The wireless communication device 200 can include a housing 210, a controller 220 coupled to the housing 210, audio input and output circuitry 230 coupled to the housing 210, a display 240 coupled to the housing 210, a transceiver 250 coupled to the housing 210, a user interface 260 coupled to the housing 210, a memory 270 coupled to the housing 210, an antenna 280 coupled to the housing 210 and the transceiver 250, and an ultraviolet sensor 295 coupled to the housing. The wireless communication device 200 can also include an ultraviolet exposure time prediction module 290. The ultraviolet exposure time prediction module 290 ultraviolet prediction module 290 can be coupled to the controller 220, can reside within the controller 220, can reside within the memory 270, can be an autonomous module, can be software, can be hardware, or can be in any other format useful for a module on a wireless communication device 200.

The display 240 can be a liquid crystal display (LCD), a light emitting diode (LED) display, a plasma display, or any other means for displaying information. The transceiver 250 may include a transmitter and/or a receiver. The audio input and output circuitry 230 can include a microphone, a speaker, a transducer, or any other audio input and output circuitry. The user interface 260 can include a keypad, buttons, a touch pad, a joystick, an additional display, or any other device useful for providing an interface between a user and an electronic device. The memory 270 may include a random access memory, a read only memory, an optical memory, a subscriber identity module memory, or any other memory that can be coupled to a wireless communication device.

In operation, the controller 220 can control the operations of the wireless communication device. The memory 270 can store personal information including skin phototype and sun protection factor information. The memory 270 can also include previous exposure information. The user interface 260, the transceiver 280, or any other input, such as a short range wireless transceiver, can obtain context related information including an activity, a location, and a time of day. The transceiver 250 can be a network interface that can retrieve environmental conditions that affect ultraviolet exposure, where the environmental conditions can include weather conditions. The ultraviolet exposure time prediction module 290 ultraviolet prediction module 290 can predict future ultraviolet exposure time, an ultraviolet index, and/or other related predictions based on the personal information, the context related information, and the environmental conditions. The ultraviolet sensor 295 can detect ultraviolet light and/or the wireless communication device 200 can receive ultraviolet light detections from other external sensors such as those attached to user accessories, coupled to other devices, and/or in a local sensor network. The ultraviolet exposure time prediction module 290 ultraviolet prediction module 290 can then predict ultraviolet exposure time based on the personal information, the context related information, the environmental conditions, and the detected ultraviolet light. The display 240 can output information corresponding to the ultraviolet exposure time.

The ultraviolet exposure time prediction module 290 ultraviolet prediction module 290 can also predict ultraviolet exposure time based on the personal information and erythemal effective radiant exposure. The erythemal effective radiant exposure can be based on solar spectral irradiance as a function of the context related information and the environmental conditions. The erythemal effective radiant exposure can also be based on erythema action spectrum, time, and a relevant wavelength. The ultraviolet exposure time prediction module 290 ultraviolet prediction module 290 can predict ultraviolet exposure time based on an ultraviolet index that is determined based on erythemal effective radiant exposure as a function of the personal information, the context related information, and the environmental conditions.

The controller 220 can detect a change in the environmental conditions during the predicted ultraviolet exposure time. The ultraviolet exposure time prediction module 290 ultraviolet prediction module 290 can then predict an updated future ultraviolet exposure time based on the personal information, the context related information, and the changed environmental conditions. Furthermore, the elements of the wireless communication device 200 can perform any of the corresponding functions illustrated in the flowcharts described in this disclosure.

Figure 3:
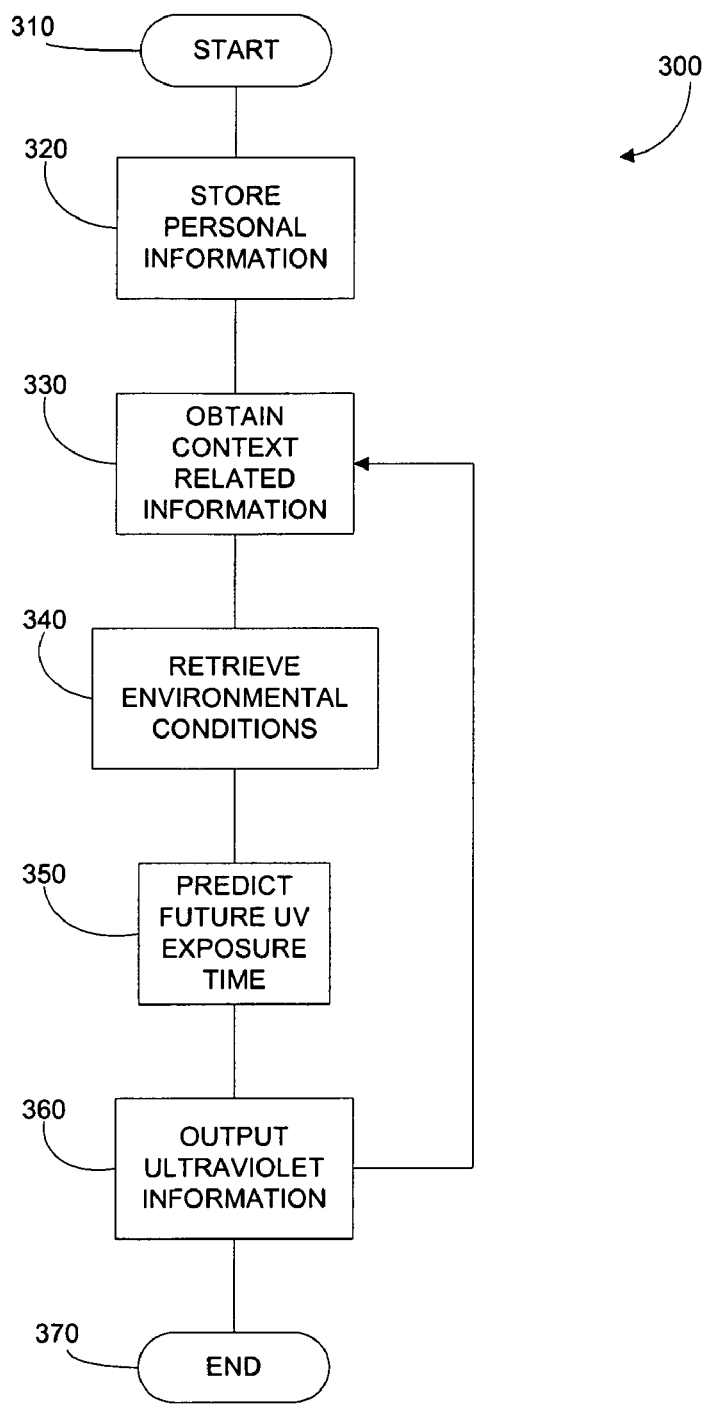
FIG. 3 is an exemplary flowchart illustrating the operation of a wireless communication device according to a possible embodiment.

FIG. 3 is an exemplary flowchart 300 illustrating the operation of the wireless communication device 200 according to another embodiment. In step 310, the flowchart begins. In step 320, the wireless communication device 200 can store, in the memory 270, personal information including skin phototype and sun protection factor information. The sun protection factor information may be set to a default or zero if it is not input or if no sun protection is worn and the skin phototype may be set to a default phototype in the memory 270. The personal information can also include previous exposure information or other personal information that relates to exposure.

In step 330, the wireless communication device 200 can obtain context related information including an activity, a location, and a time of day. The activity can include activity information indicating an outdoor activity a user is engaging in. The context related information can also include a date of the activity and altitude conditions. In step 340, the wireless communication device 200 can retrieve environmental conditions that affect ultraviolet exposure. The environmental conditions can include weather conditions that are retrieved from a network. The weather conditions can be forecast weather conditions. The environmental conditions can further include environmental surface reflectivity conditions. For example, environmental surface reflectivity conditions can include the reflectivity of environmental surfaces such as snow, ice, sand, water, grass, and/or the like.

In step 350, the wireless communication device 200 can predict ultraviolet exposure time based on the personal information, the context related information, and the environmental conditions. For example, predicting ultraviolet exposure time can include predicting permitted ultraviolet exposure time. The ultraviolet exposure time can be predicted based on erythemal effective radiant exposure as a function of the context related information and the environmental conditions.

The ultraviolet exposure time can be predicated based on personal information and erythemal effective radiant exposure. The erythemal effective radiant exposure can be based on solar spectral irradiance as a function of the context related information and the environmental conditions, and the erythemal effective radiant exposure can further be based on erythema action spectrum, time, and relevant wavelengths. The ultraviolet exposure time can be based on personal information and erythemal effective radiant exposure according to:

$$H^*_{er} = \iint E^*_\lambda \cdot s_{er}(\lambda) d\lambda dt$$

Where $H^*_{er}$ is the erythemal effective radiant exposure, where $E^*_\lambda$ is solar spectral irradiance as a function of the context related information and the environmental conditions, where $s_{er}(\lambda)$ is erythema action spectrum, where t is time, and where $\lambda$ is the relevant wavelengths. For example, $E^*_\lambda$ can be a modified solar spectral irradiance and $H^*_{er}$ can be a modified erythemal effective radiant exposure based on the factors such as variations in surface reflectivity, cloud cover, altitude, etc. In the above equation, $s_{er}(\lambda)$ can be $s_{er}(\lambda) = 1.0$ for $250 \leq \lambda \leq 298$ nm, $s_{er}(\lambda) = 10^{0.094(298-\lambda)}$ for $298 < \lambda \leq 328$ nm, and $s_{er}(\lambda) = 10^{0.015(140-\lambda)}$ for $328 < \lambda \leq 400$ nm.

The future ultraviolet exposure time can also be predicted based on an ultraviolet index that can be determined based on erythemal effective radiant exposure as a function of the personal information, the context related information, and the environmental conditions. The future ultraviolet exposure time can be predicted based on personal information and an ultraviolet index according to:

$$I^*_{UV} = k_{er} \int_{250\ nm}^{400\ nm} E^*_\lambda s_{er}(\lambda) d\lambda$$

Where $I^*_{UV}$ is ultraviolet index, where $k_{er}$ is a radiation constant value, where $E^*_\lambda$ is solar spectral irradiance as a function of the context related information and the environmental conditions, and where $s_{er}(\lambda)$ is erythema action spectrum. In the above equation, $I^*_{UV}$ can be a modified ultraviolet index that integrates the solar spectral irradiance based on the context related information and the environmental conditions.

When or after predicting the future ultraviolet exposure time, the wireless communication device 200 can detect a change in the environmental conditions during the predicted ultraviolet exposure time. The wireless communication device 200 can then predict an updated future ultraviolet exposure time based on the personal information, the context related information, and the changed environmental conditions including changed weather forecasts. Thus, the method can be dynamic in that the wireless communication device 200 can get updated information if something changes or conditions are different in real time.

In step 360, the wireless communication device 200 can output information corresponding to the ultraviolet exposure time predictions. The information corresponding to the ultraviolet exposure time can include a protection recommendation, an ultraviolet index, an exposure time recommendation, an ultraviolet index alert signal and/or an exposure alert signal. The information corresponding to ultraviolet exposure time can also correspond to an ultraviolet index. After outputting the ultraviolet information, the flowchart may return to step 330 or step 240 to obtain additional updated information to keep the predictions up to date.

The wireless communication device 200 can also receive an ultraviolet reading from a local sensor in step 340. For example, the local sensor may be located in region of activity, may be in a network of sensors, and/or may be worn by a user or may be attached to an accessory worn by a user, such as sunglasses, a mobile phone, a wireless or wired mobile phone headset, or any other accessory. Then, in step 360, the wireless communication device 200 can predict ultraviolet exposure time based on the personal information, the context related information, the environmental conditions, and the ultraviolet reading. In step 370, the flowchart 300 ends.

Figure 4:
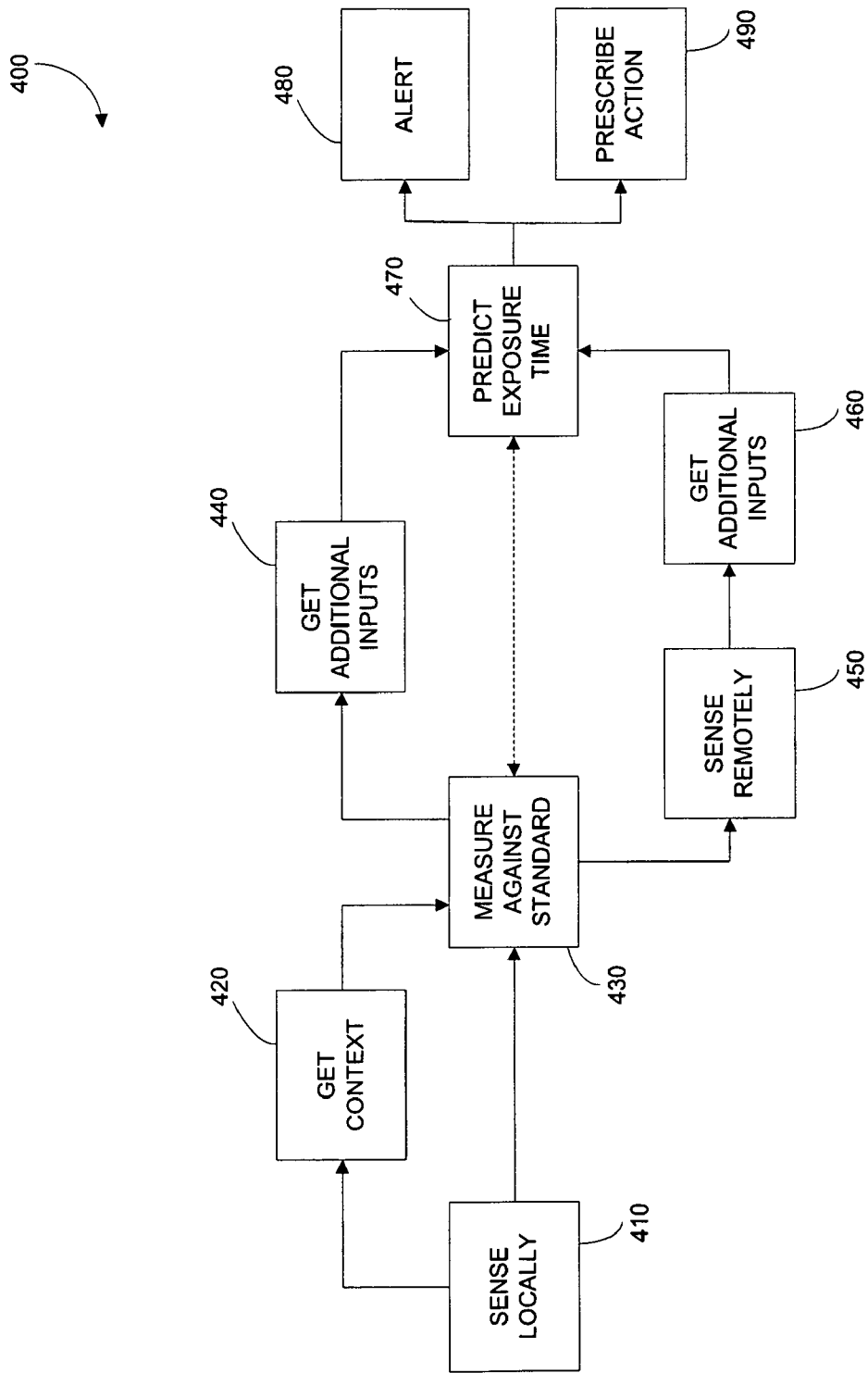
FIG. 4 is an exemplary flow diagram illustrating the operation of a wireless communication device according to another possible embodiment.

FIG. 4 is an exemplary flow diagram 400 illustrating the operation of the wireless communication device 200 according to another related embodiment. In step 410, the wireless communication device 200 can sense local conditions. For example, the wireless communication device 200 can sense local conditions using an ultraviolet sensor. In step 420, the wireless communication device 200 can get context information, such as an activity, a time, a location, or other context information. The context information may be input by a user and/or extracted from a calendar. For example, a user may have a period of time in a calendar blocked out for skiing, a beach activity, a sporting event, or any other activity. In step 430, the wireless communication device 200 can measure a determined exposure time against a standard, such as a standard established by the Occupational Safety and Health Administration (OSHA) or an International Standards Organization (ISO) standard. The exposure time may be based on skin type, a preexisting exposure time, and a current ultraviolet index. In step 440, the wireless communication device 200 can get additional inputs, such as a SPF of any sun protection worn, a skin type of a user, and/or other relevant information. These inputs can be used as multipliers for existing current local information. If remote sensing is available, in step 450, the wireless communication device 200 can sense conditions remotely, such as by getting information from sensors on other wireless communication devices and/or from sensor networks in an area of interest. In step 460, the wireless communication device 200 can get additional inputs, such as a SPF of any sun protection worn, a skin type of a user, and/or other relevant information. In step 470, the wireless communication device 200 can predict an exposure time. In step 480, the wireless communication device 200 can provide an audio, tactile, and/or visual alert if the exposure time is exceeded or close to being exceeded. In step 490, the wireless communication device 200 can prescribe action to a user, such as suggesting additional sun protection and/or suggesting moving to a shaded location.

The method of this disclosure is preferably implemented on a programmed processor. However, the controllers, flowcharts, and modules may also be implemented on a general purpose or special purpose computer, a programmed microprocessor or microcontroller and peripheral integrated circuit elements, an integrated circuit, a hardware electronic or logic circuit such as a discrete element circuit, a programmable logic device, or the like. In general, any device on which resides a finite state machine capable of implementing the flowcharts shown in the figures may be used to implement the processor functions of this disclosure.

While this disclosure has been described with specific embodiments thereof, it is evident that many alternatives, modifications, and variations will be apparent to those skilled in the art. For example, various components of the embodiments may be interchanged, added, or substituted in the other embodiments. Also, all of the elements of each figure are not necessary for operation of the disclosed embodiments. For example, one of ordinary skill in the art of the disclosed embodiments would be enabled to make and use the teachings of the disclosure by simply employing the elements of the independent claims. Accordingly, the preferred embodiments of the disclosure as set forth herein are intended to be illustrative, not limiting. Various changes may be made without departing from the spirit and scope of the disclosure.

In this document, relational terms such as "first," "second," and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a," "an," or the like does not, without more constraints, preclude the existence of additional identical elements in the process, method, article, or apparatus that comprises the element. Also, the term "another" is defined as at least a second or more. The terms "including," "having," and the like, as used herein, are defined as "comprising."

We claim:

1. A method comprising:
    storing, in a memory, personal information including skin phototype and sun protection factor information;
    obtaining context related information including an activity, a location, and a time of day;
    retrieving environmental conditions that affect ultraviolet exposure, the environmental conditions including weather conditions, where the weather conditions are retrieved from a network;
    predicting ultraviolet exposure time based on the personal information, the context related information, and the environmental conditions; and
    outputting information corresponding to the ultraviolet exposure time;
    wherein predicting ultraviolet exposure time is based on erythemal effective radiant exposure as a function of the context related information and the environmental conditions.

2. The method according to claim 1,
    wherein the environmental conditions further include environmental surface reflectivity conditions, and
    wherein the context related information includes a date of the activity and altitude conditions.

3. The method according to claim 1, further comprising receiving an ultraviolet reading from a local sensor,
    wherein predicting further comprises predicting ultraviolet exposure time based on the personal information, the context related information, the environmental conditions, and the ultraviolet reading.

4. The method according to claim 1, wherein the activity comprises activity information indicating an outdoor activity a user is engaging in.

5. The method according to claim 1, wherein the information corresponding to the ultraviolet exposure time includes one of a protection recommendation, an exposure time recommendation, an ultraviolet index alert signal, and an exposure alert signal.

6. The method according to claim 1 wherein erythemal effective radiant exposure is based on solar spectral irradiance as a function of the context related information and the environmental conditions, and erythemal effective radiant exposure is further based on erythema action spectrum, time, and relevant wavelengths.

7. The method according to claim 1, wherein predicting ultraviolet exposure time is based on personal information and erythemal effective radiant exposure according to:

$$H^*_{er} = \iint E^*_\lambda s_{er}(\lambda) d\lambda dt$$

where $H^*_{er}$ is the erythemal effective radiant exposure,
where $E^*_\lambda$ is solar spectral irradiance as a function of the context related information and the environmental conditions,
where $s_{er}(\lambda)$ is erythema action spectrum,
where t is time, and
where $\lambda$ is relevant wavelength.

8. The method according to claim 7, wherein $s_{er}(\lambda)=1.0$ for $250 \leq \lambda \leq 298$ nm, $s_{er}(\lambda)=10^{0.094(298-\lambda)}$ for $298<\lambda \leq 328$ nm, and $s_{er}(\lambda)=10^{0.015(140-\lambda)}$ for $328<\lambda \leq 400$ nm.

9. The method according to claim 1, wherein predicting future ultraviolet exposure time is based on an ultraviolet index that is determined based on erythemal effective radiant exposure as a function of the personal information, the context related information, and the environmental conditions.

10. The method according to claim 1, wherein predicting ultraviolet exposure time is based on personal information and an ultraviolet index according to:

$$I^*_{UV} = k_{er} \int_{250\ nm}^{400\ nm} E^*_\lambda s_{er}(\lambda) d\lambda$$

where $I^*_{UV}$ is ultraviolet index,
where $k_{er}$ is a radiation constant value,
where $E^*_\lambda$ is solar spectral irradiance as a function of the context related information and the environmental conditions, and
where $s_{er}(\lambda)$ is erythema action spectrum.

11. The method according to claim 1, wherein the weather conditions comprise forecast weather conditions.

12. The method according to claim 1, further comprising:
    detecting a change in the environmental conditions during the predicted ultraviolet exposure time; and predicting an updated ultraviolet exposure time based on the personal information, the context related information, and the changed environmental conditions.

13. An apparatus comprising:
- a housing;
- a controller coupled to the housing, the controller configured to control the operations of the apparatus;
- a memory coupled to the controller, the memory configured to store personal information including skin phototype and sun protection factor information;
- an input coupled to the controller, the input configured to obtain context related information including an activity, a location, and a time of day;
- a network interface coupled to the controller, the network interface configured to retrieve environmental conditions that affect ultraviolet exposure, the environmental conditions including weather conditions;
- an ultraviolet exposure time prediction module coupled to the controller, the ultraviolet exposure time prediction module configured to predict future ultraviolet exposure time based on the personal information, the context related information, and the environmental conditions; and
- a display coupled to the controller, the display configured to output information corresponding to the ultraviolet exposure time;
- wherein the ultraviolet exposure time prediction module is configured to predict ultraviolet exposure time based on an ultraviolet index that is determined based on erythemal effective radiant exposure as a function of the personal information, the context related information, and the environmental conditions.

14. The apparatus according to claim 13, wherein the network interface comprises a wireless transceiver.

15. The apparatus according to claim 13, further comprising an ultraviolet sensor coupled to the controller, the ultraviolet sensor configured to detect ultraviolet light,
wherein the ultraviolet exposure time prediction module is configured to predict ultraviolet exposure time based on the personal information, the context related information, the environmental conditions, and the detected ultraviolet light.

16. The apparatus according to claim 13,
wherein the ultraviolet exposure time prediction module is configured to predict ultraviolet exposure time based on the personal information and erythemal effective radiant exposure, and
wherein erythemal effective radiant exposure is based on solar spectral irradiance as a function of the context related information and the environmental conditions and the erythemal effective radiant exposure is also based on erythema action spectrum, time, and a relevant wavelength.

17. The apparatus according to claim 13, wherein the controller is configured to detect a change in the environmental conditions during the predicted ultraviolet exposure time, and
wherein the ultraviolet exposure time prediction module is configured to predict an updated ultraviolet exposure time based on the personal information, the context related information, and the changed environmental conditions.

18. A method comprising:
- storing, in a memory, personal information including skin type and sun protection factor information;
- obtaining context related information including activity information indicating an outdoor activity a user is engaging in, a location, a date, and a time of day;
- retrieving environmental conditions that affect ultraviolet exposure, the environmental conditions including forecast weather conditions, where the forecast weather conditions are retrieved from a network;
- predicting future ultraviolet exposure time based on personal information and erythemal effective radiant exposure, where erythemal effective radiant exposure is based on solar spectral irradiance as a function of the context related information and the environmental conditions, and erythemal effective radiant exposure is further based on erythema action spectrum, time, and a relevant wavelength; and
- outputting information corresponding to the future ultraviolet exposure time.

* * * * *